United States Patent [19]
Peglion et al.

[11] Patent Number: 5,173,490
[45] Date of Patent: Dec. 22, 1992

[54] BENZISOXAZOLE AND BENZISOTHIAZOLE COMPOUNDS

[75] Inventors: Jean-Louis Peglion, Le Vesinet; Joel Vian, Chaville, both of France

[73] Assignee: Adir et Compagnie, Courbevoie, France

[21] Appl. No.: 817,666

[22] Filed: Jan. 7, 1992

[30] Foreign Application Priority Data

Jan. 8, 1991 [FR] France ................ 91 00135

[51] Int. Cl.$^5$ .............. A61K 31/495; C07D 413/04; C07D 417/04
[52] U.S. Cl. ...................... 514/254; 544/368
[58] Field of Search ................ 544/368; 514/254

[56] References Cited

U.S. PATENT DOCUMENTS

| | | | |
|---|---|---|---|
| 3,822,267 | 7/1974 | Sorg | 544/368 |
| 4,104,387 | 8/1978 | Wade et al. | 544/368 |
| 4,104,388 | 8/1978 | Wade et al. | 544/368 |
| 4,260,610 | 4/1981 | Regnier et al. | 544/368 |
| 4,352,811 | 10/1982 | Strupczewski et al. | 546/198 |
| 4,355,037 | 10/1982 | Strupczewski et al. | 546/198 |
| 4,452,799 | 6/1984 | Temple, Jr. et al. | 544/368 |
| 4,544,663 | 10/1985 | Manning et al. | 544/368 |
| 4,812,461 | 3/1989 | Antoku et al. | 546/188 |

FOREIGN PATENT DOCUMENTS

| | | | |
|---|---|---|---|
| 0196132 | 10/1986 | European Pat. Off. | |
| 281309 | 9/1988 | European Pat. Off. | 544/368 |
| 0314098 | 5/1989 | European Pat. Off. | |
| 0329168 | 8/1989 | European Pat. Off. | |
| 353821 | 2/1990 | European Pat. Off. | 544/368 |
| 2163432 | 2/1986 | United Kingdom | 544/368 |

Primary Examiner—Cecilia Tsang
Attorney, Agent, or Firm—Gordon W. Hueschen

[57] ABSTRACT

The compounds are N-substituted N'-(benzisoxazolyl or benzisothiazolyl) piperazines useful as sedative, anxiolytic, anti-aggressive and analgesic agents and for the treatment of schizophrenia and depression.

A compound disclosed is (R,S)-3-{1-[(benzocyclobutan-1-yl)methyl]piperazin-4-yl}-6-fluoro-1,2-benzisoxazole.

13 Claims, No Drawings

BENZISOXAZOLE AND BENZISOTHIAZOLE COMPOUNDS

The present invention relates to new benzisoxazole and benzisothiazole compounds, of the formula I:

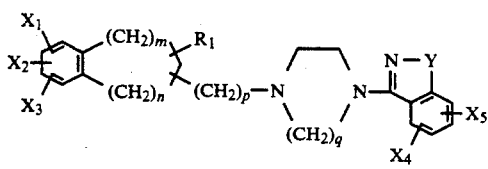

in which:

$X_1$, $X_2$, $X_3$, $X_4$ and $X_5$:
which may be the same or different, each represent:
a hydrogen atom, a halogen atom, an alkyl, alkoxy or alkylthio radical in each of which the alkyl moiety is straight-chained or branched and contains from 1 to 5 carbon atoms, a hydroxy radical, an acyloxy radical, a trifluoromethyl radical, a nitro radical, an amino radical or an acetamido radical, or
two of them in adjacent positions together form a methylenedioxy radical, an ethylenedioxy radical or a vinylenedioxy radical;
$R_1$ represents a hydrogen atom or a straight-chained or branched alkyl radical containing from 1 to 5 carbon atoms;
m and n each represent 0, 1, 2 or 3, provided that $m+n \geq 1$;
p represents 0 or an integer of from 1 to 6;
q represents 2 or 3; and
Y represents an oxygen atom or the group $S(O)_z$ in which z is 0, 1 or 2;
in racemic and optically active forms.

The prior art in this field is illustrated especially:

a) by publications relating to 1,2-benzisoxazoles or 1,2-benzisothiazoles that are substituted in the 3-position by a 4-piperidyl radical which is itself N-substituted; such compounds are described as having anti-psychotic properties—see patent applications EP 196,132, EP 314,098, and U.S. Pat. Nos. 4,352,811 and 4,812,461—or analgesic or neuroleptic properties—see U.S. Pat. Nos. 4,469,869, 4,355,037, patent application EP 080,104 and J. Med. Chem. (1985) 28, pp. 761-769;

b) or by publications relating to 1,2-benzisothiazoles that are substituted in the 3-position by an N-piperazinyl radical which is itself N'-substituted, which compounds are described as having either a non-opiate analgesic activity—see GB patent 2,163,432—or an anxiolytic or anti-psychotic activity—see especially patents EP 329,168 and BE 900,555.

However, none of these documents suggests the products of the present invention, which constitute a new class of anti-psychotic agents which are especially valuable on account of the fact that, at active doses, they are virtually harmless as regards side-effects and, especially, extra-pyramidal effects, while it is known that anti-psychotic agents can produce very considerable side-effects, which restricts their use.

The present invention relates also to the process for the preparation of the compounds of the formula I, characterised in that:
a compound of the formula II:

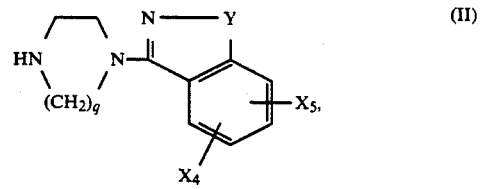

in which q, Y, $X_4$ and $X_5$ have the meanings defined above, is condensed with
a compound of the formula III:

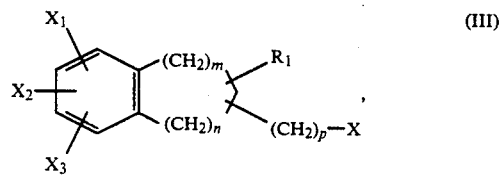

in which:
$X_1$, $X_2$, $X_3$, $R_1$, m, n and p have the meanings defined above, and
X represents a halogen atom, a mesyloxy radical or a tosyloxy radical.

It is especially appropriate to carry out the condensation in a suitable solvent, such as, for example, methyl ethyl ketone, methyl isobutyl ketone, toluene or dimethylformamide, in the presence of an acceptor for the acid formed during the reaction, at a temperature of from 20° to 150° C. There may be used as the acceptor, for example, an alkali metal carbonate, such as sodium carbonate, or a tertiary amine, such as triethylamine.

Moreover, the compounds of the formula I in which p is other than 0, that is to say the compounds corresponding more precisely to the formula I':

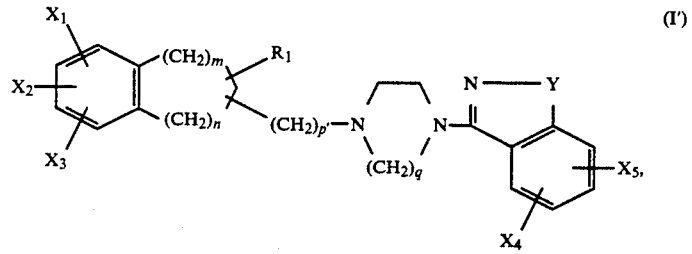

in which:
$X_1$, $X_2$, $X_3$, $X_4$, $X_5$, $R_1$, m, n, q and Y have the meanings defined above, and
p' represents an integer of from 1 to 6,
have also been prepared according to a variant of the above process, which variant is characterised in that:
a compound of the formula II defined above is condensed with:

a compound of the general formula IV:

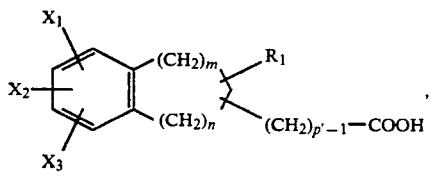

in which $X_1$, $X_2$, $X_3$, $X_4$, $X_5$, $R_1$, m, n and p' have the meanings defined above; and the resulting amide of the formula V:

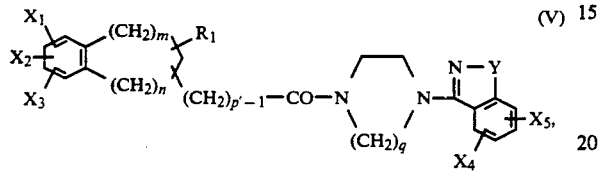

in which $X_1$, $X_2$, $X_3$, $X_4$, $X_5$, $R_1$, m, n, p', q and Y have the meanings defined above, is reduced.

It is especially appropriate to carry out the condensation of the compounds II and IV in a suitable solvent, such as, for example, methylene chloride, in the presence of carbonyldiimidazole.

The amide V is advantageously reduced by means of a double hydride of lithium and aluminium in a suitable solvent, such as, for example, ether or tetrahydrofuran.

The latter process for the preparation of the compounds I' is likewise included in the present invention.

Moreover, the amides of the general formula V are new intermediates which, as such, form part of the present invention.

The starting amines of the general formula II were prepared analogously to the synthesis described by J. P.. YEVICH et al., J. Med. Chem. (1986), 29, 359-369.

The starting materials of formulae III and IV are either known products or products prepared from known compounds, according to known methods, as indicated in the Examples below.

The compounds of the general formula I yield salts with physiologically tolerable acids. Those salts are likewise included in the present invention.

The compounds of the present invention have valuable pharmacological and therapeutic properties. In fact, pharmacological tests have shown that the compounds of the invention are antagonists of dopamine and serotonin and have an anti-psychotic activity comparable to that of haloperidol or chlorpromazine, which are reference compounds used for the evaluation of anti-psychotic agents. Moreover, at active doses they induce only few side-effects and, in particular, few extra-pyramidal effects.

It is known that anti-psychotic agents generally produce very considerable side-effects, which restricts their use. The compounds of the invention therefore constitute a new class of anti-psychotic agents which can be used for the treatment of schizophrenia and depression. They may also be used as sedative, anxiolytic, anti-aggressive and analgesic agents.

The present invention relates also to pharmaceutical compositions containing as active ingredient a compound of the general formula I or a physiologically tolerable salt thereof, in admixture or in association with a suitable pharmaceutical excipient, such as, for example, glucose, lactose, talc, ethylcellulose, magnesium stearate or cocoa butter.

The pharmaceutical compositions so obtained are generally in dosage unit form and may contain from 0.5 to 100 mg of active ingredient. They may be in the form of, for example, tablets, dragees, soft gelatin capsules, suppositories or injectable or drinkable solutions, and may be administered orally, rectally or parenterally, as appropriate, at a dose of from 0.5 to 100 mg of active ingredient from 1 to 3 times per day.

The following Examples illustrate the present invention, melting points being determined using a Kofler hot-plate under a microscope.

EXAMPLE 1

(R,S)-3-{1-[(benzocyclobutan-1-yl)methyl]piperazin-4-yl}-6-fluoro-1,2-benzisoxazole

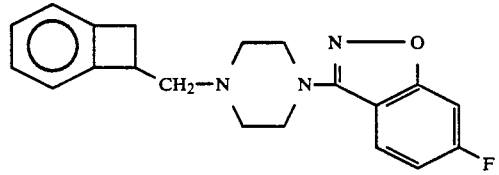

4 g ($16 \times 10^{-3}$ mol) of (benzocyclobutan-1-yl)methyl iodide, 3.6 g ($16 \times 10^{-3}$ mol) of N-(6-fluoro-1,2-benzisoxazol-3-yl)piperazine, 3.5 g ($32 \times 10^{-3}$ mol) of $Na_2CO_3$ and 70 ml of methyl isobutyl ketone are mixed, and the whole is heated at 80° C. for 12 hours, with stirring. The reaction mixture is concentrated using a rotary evaporator and the concentrate is taken up in ethyl acetate. After washing with water, the organic phase is extracted several times with a normal hydrochloric acid solution. The aqueous phase is rendered alkaline and then extracted with $CH_2Cl_2$. Drying and chromatography over silica using a methylene chloride/methanol mixture, 95/5, as eluant yield 0.65 g of a solid product. The latter is dissolved in 10 ml of ethanol, 0.65 ml of 3N ethyl chloride are added, and the whole is left to precipitate for one night. 0.55 g of (R,S)-3-{1-[(benzocyclobutan-1-yl)-methyl]piperazin-4-yl}-6-fluoro-1,2-benzisoxazole hydrochloride is collected.

m.p.: 246°-250° C. (with sublimation at about 190° C.).

Yield: 9%.

NMR (solvent: DMSO d6) unresolved peak exchangeable by $D_2O$ at 11.6 ppm; 8.15 ppm, 1 H (dd); 7.6 ppm, 1 H (dd); 7.1 to 7.3 ppm, 5 H (m); 4 to 4.3 ppm, 2 H (d broad)+1 H (m); 3.1 to 3.8 ppm, 10 H (m).

The (benzocyclobutan-1-yl)methyl iodide used as starting material was prepared as follows: 6 g of benzocyclobutan-1-ylmethyl para-toluenesulphonate [prepared according to the process described in JACS (1975), 154, p. 347] are mixed with 6.2 g of sodium iodide in 85 ml of acetone. The reaction medium is refluxed for 8 hours and then poured onto 150 ml of water and extracted several times with diethyl ether. The organic phase is then washed with a normal sodium thiosulphate solution, dried over anhydrous magnesium sulphate and concentrated, yielding (benzocyclobutan-1-yl)methyl iodide in the form of an oil.

Yield: 88%.

Proton NMR spectrum (solvent: $CDCl_3$): 2.85 ppm, d, 1 H; 3.3 to 3.6 ppm, m, 3 H; 3.9 ppm, m, 1 H; 7 to 7.3 ppm, m, 4 H.

The N-(6-fluoro-1,2-benzisoxazol-3-yl)piperazine used as starting material was prepared according to J. P. YEVICH et al., J. Med. Chem. (1986) 29, pp. 359–369.

The compounds of Examples 2 and 3 were prepared in the same manner:

EXAMPLES 2 and 3

2) (R,S)-3-{1-[4-(benzocyclobutan-1-yl)butyl]piperazin-4-yl}-1,2-benzisothiazole and its hydrochloride, m.p. (instantaneous): 202° C., from 4-(benzocyclobutan-1-yl)butyl bromide and N-(1,2-benzisothiazol-3-yl)piperazine.

3) (R,S)-3-{1-[2-(benzocyclobutan-1-yl)ethyl]piperazin-4 -yl}-1,2-benzisothiazole and its hydrochloride, m.p. (instantaneous): 222° C., from 2-(benzocyclobutan-1-yl)ethyl bromide and N-(1,2-benzisothiazol-3-yl)piperazine.

EXAMPLE 4

(R,S)-3-{1-[(benzocyclobutan-1-yl)methyl]piperazin-4-yl}-1,2-benzisothiazole

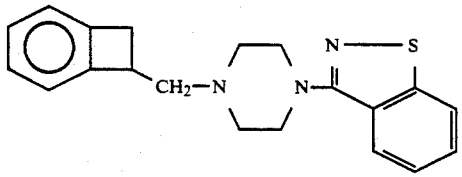

A mixture of 2.5 g of (benzocyclobutan-1-yl)methyl tosylate [prepared according to the process described in JACS (1975) 154, p. 37], 1.9 g of N-(1,2-benzisothiazol-3-yl)piperazine [prepared according to J. P.. YEVICH et al., J. Med. Chem. (1986), 29, pp. 359–369] and 1.3 ml of triethylamine in 25 ml of toluene is brought to reflux and kept under reflux for 18 hours. After cooling, 25 ml of ethyl acetate and 20 ml of 20% sodium hydroxide solution are added. After separating off, the organic phase is dried and evaporated to dryness. The resulting residue is chromatographed over 300 g of silica using a methylene chloride/ethyl acetate mixture (90/10) as eluant. 1.4 g of product are obtained (yield: 40%); the product is introduced into 5 ml of acetonitrile, and then 3 ml of ethyl chloride are added thereto, yielding (R,S)-3-{1-[(benzocyclobutan-1-yl)methyl]piperazin-4-yl}-1,2-benzisothiazole dihydrochloride, m.p.: 208°–215° C. (with slow sublimation from 170°C.).

NMR (solvent: DMSO d6): 8.15 ppm, m, 2 H; 7.4 to 7.6 ppm, m, 2 H; 7 to 7.3 ppm, m, 4 H; 4 to 4.2 ppm, d+m, 3 H; 3.2 to 3.8 ppm, m+d+m+ n+m=9 H; 3.15 ppm, d, 1 H; 11.5 ppm, 2 H exchangeable.

The compounds of Examples 5 to 16 were prepared in the same manner.

EXAMPLES 5 to 16

5) (R,S)-3-{1-[(benzocyclobutan-1-yl)methyl]homopiperazin-4-yl}-1,2-benzisothiazole and its di-(dibenzoyltartrate), m.p.: 110°14 115° C. (yield: 52.7%), from (benzocyclobutan-1-yl)methyl tosylate and N-(1,2-benzisothiazol-3-yl)homopiperazine [prepared according to J. P. YEVICH et al., J. Med. Chem. (1986), 29, 359–369].

6) (R,S)-3-{1-[(benzocyclobutan-1-yl)methyl]piperazin-4-yl}-1,2-benzisoxazole and its hydrochloride, m.p.: 239°–243° C. (with sublimation from 190° C.) (yield: 11%), from (benzocyclobutan-1-yl)methyl tosylate and N-(1,2-benzisoxazol-3-yl)piperazine.

7) (R,S)-3-{1-[(indan-1-yl)methyl]piperazin-4-yl}-1,2-benzisothiazole, m.p.: 88°–90° C. (yield: 30%), from (indan-1-yl)methyl tosylate and N-(1,2-benzisothiazol-3-yl)piperazine.

8) (R,S)-3-{1-[(5,6-dimethoxyindan-1-yl)methyl]piperazin-4-yl}-1,2-benzisothiazole, m.p.: 131°–133° C. (yield: 3.6%), from (5,6-dimethoxyindan-1-yl)methyl tosylate and N-(1,2-benzisothiazol-3-yl)piperazine.

The (5,6-dimethoxyindan-1-yl)methyl tosylate used as starting material was prepared as follows:

To 3.1 g of lithium aluminium hydride suspended in 30 ml of tetrahydrofuran there are added 18 g of (5,6-dimethoxyindan-1-yl)carboxylic acid [described in J. Pharm. Sci. (1968) 57 (6) 1013] dissolved in 180 ml of tetrahydrofuran. After stirring at room temperature for 18 hours, there are added dropwise, with cooling, 2.2 ml of water, then 1.7 ml of 20% sodium hydroxide, and finally 7.6 ml of water. The mineral salts are then filtered and rinsed, and the filtrate is evaporated to dryness. In this manner, 16.5 g of (5,6-dimethoxyindan-1-yl)methanol are obtained in the form of an oil, in a yield of 98%.

NMR (solvent: CDCl₃): 6.8 ppm, s, 2 H; 3.9 ppm, s, 6 H; 3.8 ppm, d, 2 H; 3.3 ppm, m, 1 H; 2.9 ppm, m, 2 H; 2.3 ppm, m, 1 H; 2 ppm, m, 1 H; 1.8 ppm, 1 H exchangeable.

23.7 g of p-toluenesulphonyl chloride are added to the 16.5 g of alcohol obtained above dissolved in 100 ml of pyridine. After stirring at room temperature for 18 hours, the reaction medium is concentrated in vacuo. The resulting residue is taken up in methylene chloride and then washed with normal sulphuric acid. After separating off, the organic phase is dried and then evaporated to dryness. 31 g of (5,6-dimethoxyindan-1-yl)methyl tosylate are obtained in the form of an oil, in a yield of 97.5%.

NMR (solvent: CDCl₃): 7.7 ppm, d, 2 H; 7.3 ppm, d, 2 H; 6.7 ppm, 2s, 2 H; 3.9 to 4.3 ppm, m, 2 H; 3.8 ppm, 2 s, 6 H; 3.5 ppm, m, 1 H; 2.8 ppm, m, 2 H; 2.4 ppm, s, 3 H; 2.25 ppm, m, 1 H; 1.8 ppm, m, 1 H.

9) 3-[1-(indan-2-yl)piperazin-4-yl]-1,2-benzisothiazole, m.p.: 158°–162° C., from indan-2-yl tosylate and N-(1,2-benzisothiazol-3-yl)piperazine.

10) 3-[1-(indan-2-yl)piperazin-4-yl]-1,2-benzisoxazole and its fumarate, m.p.: 216°–219° C., from indan-2-yl tosylate and N-(1,2-benzisoxazol-3-yl)piperazine.

11) 3-[1-(indan-2-yl)piperazin-4-yl]-6-fluoro-1,2-benzisoxazole and its fumarate, m.p.: 205°–208° C., from indan-2-yl tosylate and N-(6-fluoro-1,2-benzisoxazol-3-yl)piperazine.

12) (R,S)-3-{1-[(4,5-dimethoxybenzocyclobutan-1-yl)-methyl]piperazin-4-yl}-1,2-benzisothiazole and its hydrochloride, m.p.: >260° C., from (4,5-dimethoxybenzocyclobutan-1-yl)methyl tosylate and N-(1,2-benzisothiazol-3-yl)piperazine.

13) (R,S)-3-{1-[3-(benzocyclobutan-1-yl)propyl]piperazin-4-yl}-1,2-benzisothiazole and its hydrochloride, m.p.: >260° C., from 3-(benzocyclobutan-1-yl)propyl mesylate and N-(1,2-benzisothiazol-3-yl)piperazine.

14) (R,S)-3-{1-[2-(4,5-dimethoxybenzocyclobutan-1-yl)ethyl]piperazin-4-yl}-1,2-benzisothiazole and its hydrochloride, m.p.: 198°–200° C., from 2-(4,5-dimethoxybenzocyclobutan-1-yl)ethyl tosylate and N-(1,2-benzisothiazol-3-yl)piperazine.

15) 3-{1-[(5,6-dimethoxyindan-2-yl)methyl]piperazin-4-yl}-1,2-benzisothiazole, m.p.: 102°–105° C., from (5,6- dimethoxyindan-2-yl)methyl tosylate and N-(1,2-benzisothiazol-3-yl)piperazine.

16) 3-{1-[(indan-2-yl)methyl]piperazin-4-yl}-1,2-benzisothiazole, m.p.: 88°-90° C., from (indan-2-yl)methyl tosylate and N-(1,2-benzisothiazol-3-yl)piperazine.

EXAMPLE 17

(R,S)-3-{1-[(4,5-dimethoxybenzocyclobutan-1-yl)methyl]-piperazin-4-yl}-6-fluoro-1,2-benzisoxazole

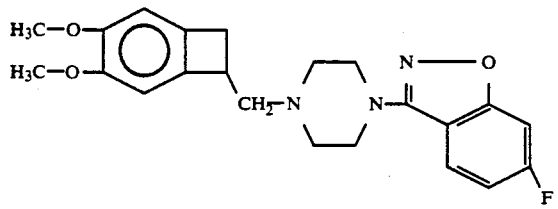

a) First step:

2.12 g ($1.02 \times 10^{-2}$ mol) of (4,5-dimethoxybenzocyclobutan-1-yl)carboxylic acid are mixed in 12 ml of methylene chloride, and 1.72 g ($1.06 \times 10^{-2}$ mol) of carbonyldiimidazole are added in a single batch. The whole is stirred at room temperature for one night, and then 2.26 g ($1.02 \times 10^{-2}$ mol) of N-(6-fluoro-1,2-benzisoxazol-3-yl)piperazine [prepared according to J. P. YEVICH et al., J. Med. Chem. (1986), 29, pp. 359-369] are added by means of a spatula.

The reaction mixture is left at room temperature for 48 hours, and then water is added. After separating off, the organic phase is washed with water and then with an $NaHCO_3$ solution. Drying yields a gum, which is crystallised from ethyl acetate, yielding 2.4 g of (R,S)-3-{1-[(4,5-dimethoxybenzocyclobutan-1-yl)carbonyl]piperazin-4-yl}-6-fluoro-1,2-benzisoxazole, m.p.: 200° C.

Yield: 57%.

NMR (solvent: $CDCl_3$): 7.65 ppm, 1 H (dd); 7.15 ppm, 1 H (dd); 7.05 ppm, 1 H (td); 6.7 to 6.8 ppm, 2 H (2 s); 4.4 ppm, 1 H (t); 3.7 to 4 ppm, 4 H (m)+6 H (2 s); 3.65 ppm, 4 H (m); 3.4 ppm, 2 H (d).

The (4,5-dimethoxybenzocyclobutan-1-yl)carboxylic acid used as starting material was prepared according to the process described in Tetrahedron (1973), 29, p. 73.

b) Second step:

Under a nitrogen atmosphere, 0.26 g ($7 \times 10^{-3}$ mol) of lithium aluminium hydride are added to 41 ml of anhydrous tetrahydrofuran. The whole is heated to 30° C. and then 2.4 g ($5.8 \times 10^{-3}$ mol) of (R,S)-3-{1-[(4,5-dimethoxybenzocyclobutan-1-yl)carbonyl]piperazin-4-yl}-6-fluoro-1,2-benzisoxazole, obtained above, are added by means of a spatula. The temperature of the reaction mixture is kept at 30° C. for 8 hours. The whole is then cooled and hydrolysed with 0.9 ml of water and 0.15 ml of 20% sodium hydroxide solution. After filtration of the salts and separating off the reaction mixture, the organic phase is washed with water and then dried over $MgSO_4$. Chromatography over silica using a methylene chloride/ethyl acetate mixture (90/10) as eluant, and recrystallisation from 4.5 ml of ethyl acetate yield 0.63 g of (R,S)-3-{1-[(4,5-dimethoxybenzocyclobutan-1-yl)methyl]piperazin-4-yl}-6-fluoro-1,2-benzisoxazole, m.p.: 141°-143° C., yield: 27%.

NMR (solvent: $CDCl_3$): 7.65 ppm, 1 H (dd); 7.15 ppm, 1 H (dd); 6.95 ppm, 1 H (td); 6.7 ppm, 2 H (2 s); 3.85 ppm, 6 H (s); 3.6 ppm, 5 H (m); 3.3 ppm, 1 H (dd); 2.6 to 3 ppm, 1 H (dd)+2 H (m)+4 H (m).

The compounds of Examples 18 to 20 were prepared in the same manner:

EXAMPLES 18 to 20

18) (R,S)-3-{1-[(indan-1-yl)methyl]piperazin-4-yl}-6-fluoro-1,2-benzisoxazole, m.p.: 109°-111° C. (yield: 28%), from (R,S)-3-{1-[(indan-1-yl)carbonyl]piperazin-4-yl}-6-fluoro-1,2-benzisoxazole, m.p.: 151° C., which was itself prepared, in a yield of 55%, from indan-1-ylcarboxylic acid and N-(6-fluoro-1,2-benzisoxazol-3-yl)piperazine.

19) (R,S)-3-{1-[(4,5-dimethoxybenzocyclobutan-1-yl)-methyl]piperazin-4-yl}-1,2-benzisoxazole, m.p.: 136°-139° C. (yield: 52%), from (R,S)-3-{1-[(4,5-dimethoxybenzocyclobutan-1-yl)carbonyl]piperazin-4-yl}-1,2-benzisoxazole, m.p.: 165° C., which was itself prepared, in a yield of 80%, from (4,5-dimethoxybenzocyclobutan-1-yl)carboxylic acid and N-(1,2-benzisoxazol-3-yl)piperazine.

20) (R,S)-3-{1-[(indan-1-yl)methyl]piperazin-4-yl}-1,2-benzisoxazole, m.p.: 83°-86° C. (yield: 44%), from (R,S)-(3-{1-[(indan-1-yl)carbonyl]piperazin-4-yl}-1,2-benzisoxazole, m.p.: 114° C., which was itself prepared, in a yield of 80%, from indan-1-ylcarboxylic acid and N-(1,2-benzisoxazol-3-yl)piperazine.

EXAMPLE 21

Pharmacological Study

Test of the Stereotypies Induced By Methyl Pohenidate in Rats 24 male Wistar rats which weighed between 220 and 240 g and which had eaten nothing for approximately 24 hours were used for this test. Each animal receives a first treatment (reference compound, compound of the invention, or solvent) at a given time before a second treatment (methyl phenidate or physiological serum), which is effected by the i.p. route at the time designated $T_0$. Among the animals used for a test, four serve as control and receive the following treatments: serum+-serum i.p.: 1 animal (serum control); solvent+ 40 mg/kg i.p. methyl phenidate: 2 animals (40 mg/kg i.p. methyl phenidate control); and solvent+0.16, 0.63, 2.5 or 10 mg/kg i.p. of methyl phenidate: 1 animal (0.16, 0.63, 2.5 or 10 mg/kg i.p. methyl phenidate controls).

The test products were administered at given times before the injection of 40 mg/kg i.p. of methyl phenidate at $T_0$. Each animal is observed for a period of 10 seconds. Observations of behaviour were carried out 30 minutes after the treatment with methyl phenidate. A total of 10 observation periods is carried out for each rat at time $T_{30 \text{min}}$. During these observations, the presence (1) or absence (0) of stereotypy is noted.

The statistical analysis consisted in comparing, for a given stereotypy, the scores (0 to 10) obtained for a group of animals that had received the same treatment with those obtained for the 40 mg/kg methyl phenidate control group of animals, according to the Mann and Whitney test, with significance $p = 0.05$ (cf. Siegel S. and Castelan N.J., 1988).

By way of an example of the evaluation of the antipsychotic activity of the products of the present invention, the mean effective doses ($ED_{50}$), that is to say the doses permitting inhibition of bruxism by 50%, are listed in the Table below.

| Products of Examples nos. | ED$_{50}$ (mg/kg i.p.) |
| --- | --- |
| 1 | 0.31 |
| 4 | 10 |
| 6 | 1.25 |
| 17 | 2.5 |
| 18 | 10 |
| 19 | 1.25 |
| chlorpromazine | 1.4 |

We claim:

1. A compound selected from the group consisting of: benzisoxazole and benzisothiazole compounds of formula I:

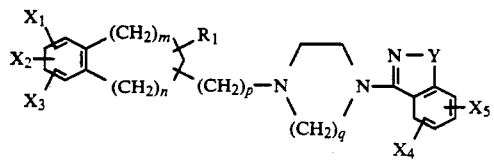

in which:

$X_1$, $X_2$, $X_3$, $X_4$ and $X_5$:
  which are the same or different, each represent: hydrogen, halogen, alkyl, alkoxy, or alkylthio in each of which the alkyl moiety is straight-chained or branched and contains 1 to 5 carbon atoms, inclusive, hydroxy, carboxylic acid, acyloxy, trifluoromethyl, nitro, amino, or acetamido, or
  two of them in adjacent positions together form methylenedioxy, ethylenedioxy, or vinylenedioxy;

$R_1$ represents hydrogen or straight-chained or branched alkyl containing 1 to 5 carbon atoms, inclusive;

m and n each represent 0, 1, 2, or 3, provided that $m+n \geq 1$;

p represents 0 or an integer of 1 to 6 inclusive;

q represents 2 or 3; and

Y represents oxygen or $S(O)_z$ in which z is 0, 1, or 2;
in racemic and optically active forms, and the physiologically-tolerable acid addition salts thereof.

2. A compound of claim 1 which is selected from: (R,S)-3-{1-[(benzocyclobutan-1-yl)methyl]piperazin-4-yl}-6-fluoro-1,2-benzisoxazole and the physiologically-tolerable acid addition salts thereof.

3. A compound of claim 1 which is selected from: (R,S)-3-{1-[(benzocyclobutan-1-yl)methyl]piperazin-4-yl}-6-fluoro-1,2-benzisoxazole and its hydrochloride.

4. A compound of claim 1 which is selected from: (R,S)-3-{1-[4-(benzocyclobutan-1-yl)butyl]piperazin-1-yl}-1,2-benzisothiazole and its hydrochloride.

5. A compound of claim 1 which is selected from: (R,S)-3-{1-[(benzocyclobutan-1-yl)methyl]piperazin-4-yl}-1,2-benzisoxazole and its hydrochloride.

6. A compound of claim 1 which is selected from: 3-[1-(indan-2-yl)piperazin-4-yl]-6-fluoro-1,2-benzisoxazole and its fumarate.

7. A compound of claim 1 which is selected from: (R,S)-3-{1-[3-(benzocyclobutan-1-yl)propyl]piperazin-4-yl}-1,2-benzisothiazole and its hydrochloride.

8. A compound of claim 1 which is: 3-{1-[(5,6-dimethoxyindan-2-yl)methyl]piperazin-4-yl}-1,2-benzisothiazole.

9. A compound of claim 1 which is: (R,S)-3-{1-[(4,5-dimethoxybenzocyclobutan-1-yl)methyl]piperazin-4-yl}-6-fluoro-1,2-benzisoxazole.

10. A compound of claim 1 which is: (R,S)-3-{1-[(4,5-dimethoxybenzocyclobutan-1-yl)methyl]piperazin-4-yl}-1,2-benzisoxazole.

11. A pharmaceutical composition useful to treat psychosis and anxiety containing as active ingredient an effective amount of a compound of claim 1 together, with one or more pharmaceutically-acceptable excipients.

12. A method for treating a living animal afflicted with anxiety and psychosis, or comprising the step of administering to the said living animal an amount of a compound of claim 1 which is effective for the alleviation of the said condition.

13. As a intermediate, an amide compound of formula V:

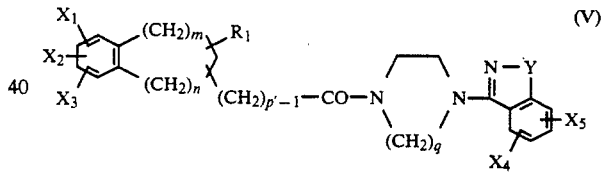

in which:

$X_1$, $X_2$, $X_3$, $X_4$, $X_5$, $R_1$, m, n, p′, q and Y have the meanings defined in claim 1 and p′ is 1–6 inclusive.

* * * * *